United States Patent [19]

Westerman

[11] 4,402,671
[45] Sep. 6, 1983

[54] METHOD AND APPARATUS FOR DENTAL CROWN REMOVAL

[76] Inventor: Robert D. Westerman, 7931 Jefferson Hwy., Baton Rouge, La. 70809

[21] Appl. No.: 379,259

[22] Filed: May 17, 1982

[51] Int. Cl.³ .......................... A61C 5/08; A61C 3/08
[52] U.S. Cl. .................................... 433/218; 433/152
[58] Field of Search .............. 433/161, 152, 158, 218, 433/219

[56] References Cited

U.S. PATENT DOCUMENTS 2,591,451  4/1952  Lynch et al. ...................... 433/152
2,640,266  6/1953  Sarti ................................... 433/152

Primary Examiner—Robert Peshock
Attorney, Agent, or Firm—Abraham Friedman

[57] ABSTRACT

A removal dental crown adapted to be secured by a layer of bonding material to a tooth. The crown has a removable key threadedly secured in a channel formed directly in the crown. The key includes a recess for receiving a tool for removal of the key thereby leaving a threaded channel in the crown. An extractor tool can then be inserted into the threaded channel for engagingly breaking the bonding layer and forcing the crown away from the tooth.

14 Claims, 20 Drawing Figures

METHOD AND APPARATUS FOR DENTAL CROWN REMOVAL

BACKGROUND OF THE INVENTION

This invention relates to dental prosthesis such as crowns, bridges, or splints, and more particularly to a method and apparatus for removal of such prosthesis from teeth without damaging either the prosthesis or the teeth.

It is often necessary for a dentist to remove a crown or bridge that has been fixed in place on the teeth. For example, occasionally a problem arises in connection with the crown itself or the joining between the crown and the tooth. Leakage could occur, the crown could break or other things could occur. Occasionally, the crown must be removed for providing access to the teeth when further dental work is needed on the underlying teeth.

Another occasion requiring removal of the crown is when the prosthesis has been placed on a patient, especially on a young patient where the restoration is not necessarily one that will last a lifetime.

One method that has been utilized in the past is to cut a slice through the metal material on every abutment. This process is extremely time consuming and costly since the prosthesis is wasted. Another method has been to attempt to break the crown loose from the dental tooth using a mallet, chisel or the like. This procecure often fractures the tooth and is an extremely painful experience for the patient.

U.S. Pat. No. 3,747,215 describes another method which includes the casting of a sleeve directly in the crown. The sleeve is retained by means of laterally extending lugs which fit within the crown material. Internally of the sleeve is a threaded hole which receives a closure screw during actual utilization of the crown in the mouth. When removal of the crown is required, the closure screw is removed and replaced with a jack screw long enough to extend through the threaded hole within the sleeve so that it breaks the bond between the crown and the tooth as the jack screw is continuously threaded into the sleeve.

While this prior method is an improvement over prior art approaches, it requires that the crown be initially formed with the sleeve in it. Accordingly, it is not suitable for those situations where existing crowns are present in the mouth or where a crown has been prepared by a laboratory without the sleeve cast within it. Additionally, in most cases, the crown requires further adjustments upon installation in the mouth. Such adjustment frequently requires reduction in the occlusal anatomy of the crown during the fitting or seating process. With the sleeve cast within the crown and extending through the occlusal surface, it is not possible to reduce the occlusal height of the tooth since this would then destroy the ability of the sleeve to receive the closure screw therein. Also, the shape of the tooth anatomy is such that in many cases a crown must be placed on an anterior tooth, a posterior tooth, awkward shaped occlusal anatomies, etc. The sleeve could not be modified to accommodate an incline or angled upper surface. Also, using this method, a recessed area of the threaded portion necessitates a much larger system on the occlusal surface making it less aesthetic and requiring a flatter horizontal area. Also, it is difficult to obtain an absolute fit between the various portions of this system.

Accordingly, there is need for an improved method and appatatus for removing dental crowns. It should be appreciated, that hereinafter, the term dental crown will refer to all types of prosthesis capable of utilizing this system including crowns, bridges, splints, etc.

SUMMARY OF THE INVENTION

Accordingly, it is an object of the present invention to provide a removable dental crown which avoids the aforementioned problems of prior art devices. Another object of the present invention is to provide a removal dental crown which has a removal key threadedly secured in a channel in the crown which can be selectively removed to accommodate an extraction tool for removing the crown from the tooth.

Another object of the present invention is to provide a unique key for insertion in a dental crown to facilitate removal of such dental crown.

Another object of the present invention is to provide a method for removing a dental crown.

A further object of the present invention is to provide a kit useful for removing a dental crown.

Briefly, in accordance with the present invention, there is provided a removable dental crown adapted to be secured by a layer of bonding material to a tooth. The crown has a removable key threadedly secured in a channel formed directly in the crown. The key includes a recess for receiving a removal tool for removing the key thereby leaving the threaded channel in the crown. An extracting tool is then threaded into the channel for engagingly breaking the bonding layer and forcing the crown away from the tooth.

In an embodiment of the invention, the key comprises a set screw having a wrench receiving indented recess therein.

The invention further contemplates a method of removing a dental crown secured by a layer of bonding material to a tooth. The method includes the steps of forming a channel directly into the dental crown and tapping the channel in the crown. Then, an extracting tool is threaded into the tapped channel until the bonding layer between the tooth and crown breaks, thereby freeing the crown from the tooth.

In an embodiment, a key is inserted into the tapped channel and is retained in place until removal of the crown is desired, at which time the key is removed by means of a removal tool.

The invention also contemplates a kit for removing a dental crown. The kit includes at least one channel twist drill for forming a channel directly into the crown. Also included is a tap for threading the channel and an assortment of keys for insertion into the threaded channel to plug up the channel during utilization of the crown. A key wrench is also included for withdrawing the key when removal of the crown is desired. An extracting tool is provided for threading into the channel until it engages the tooth so as to break the bonding layer and force the crown from the tooth.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings.

In the various figures of the drawing, like reference characters designate like parts.

DESCRIPTION OF THE PREFERRED EMBODIMENTS

The present invention permits the removal of a dental crown by the formation of a threaded channel in the crown. The threaded channel can be filled with a key during such time as the crown is installed in place on the teeth. When it is desired to remove the crown, a key wrench is used to withdraw the key leaving the threaded channel in the crown. An extractor is then threaded into the channel and presses against the body of the tooth. Continued rotation of the extractor forces the crown to break the connection with the tooth and is then removed from the tooth.

The key can be cast directly into the crown during actual laboratory construction. However, if the prosthesis is returned from the laboratory without the key, insertion of the key can be done directly in the office where the channel is formed, tapped, and the key inserted into the channel.

Even when the crown has been initially cast and installed without the key, it is still possible to remove the crown by forming a pilot hole drilled into the crown followed by the drilling of a larger hole to form a channel. The channel is then threaded by means of a tap. The extractor is then inserted into the threaded channel and upon sufficient rotation forces the crown to separate from the tooth body. When replacement of the crown occurs, the key is then inserted into the threaded channel to plug the channel.

Figure 1:
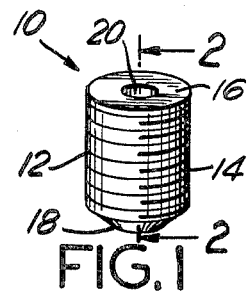
FIG. 1 is a perspective view of a key utilized in connection with the removal apparatus of the present invention.
Figure 2:
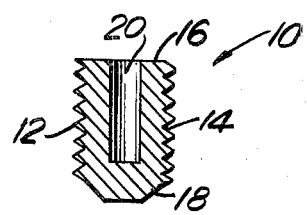
FIG. 2 is a sectional view taken along line 2—2 of FIG. 1.
Figure 3:
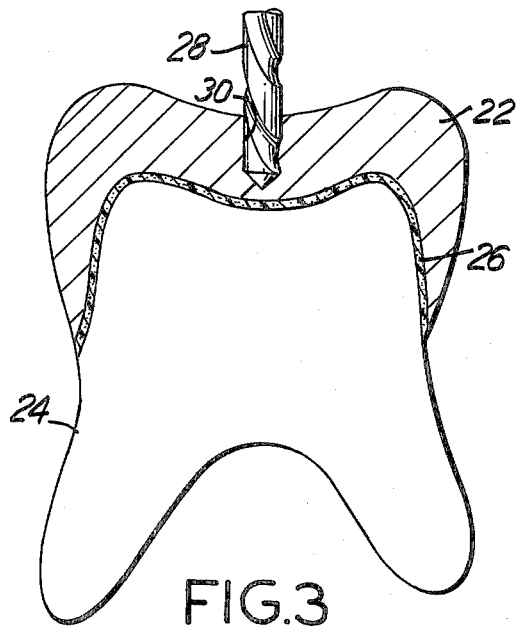
FIGS. 3-6 show various steps in the removal of a dental crown in accordance with the present invention and wherein the dental crown was initially installed without the removal capabilities of the present invention.
Figure 4:
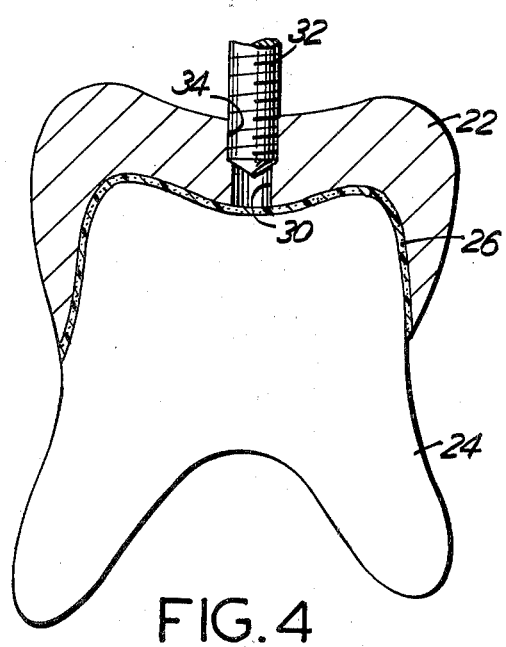
Figure 5:
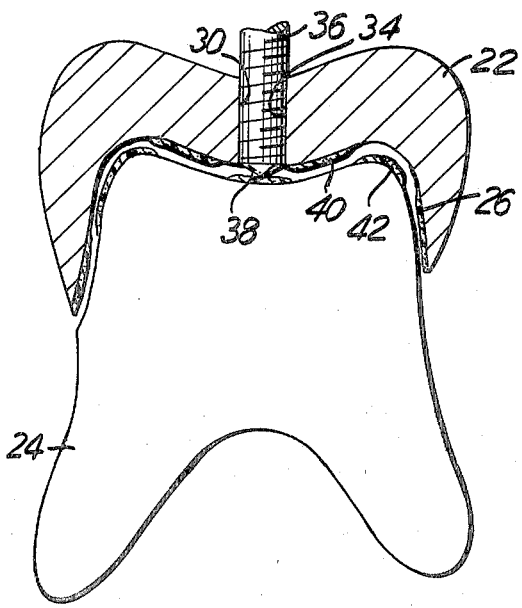
Figure 6:
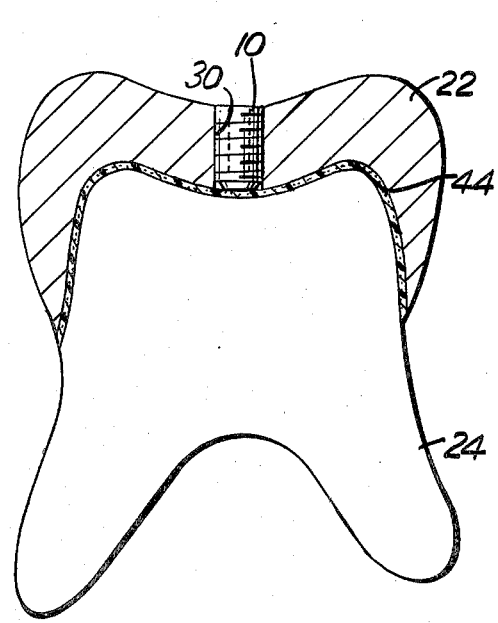

Referring now to FIGS. 1 and 2, the key utilized is shown at 10 and is formed as a set screw. It includes a substantially cylindrical body portion 12 which is externally threaded at 14. The threading is entirely from its top flat surface 16 to its lower conical end 18. Formed axially through the top surface 16 and extending downward through the body portion is a recess 20 in which a wrench can be inserted for manipulating the key. The particular shape of the recess can be any of numerous types so as to accommodate a hex, spline, torx, or any other configuration in order to manipulate the key.

Referring now to FIGS. 3-6, a method will be described where a crown has been initially installed without availability for removal. As shown, a metal crown 22 has been bonded onto a tooth 24 by means of a bonding layer 26. Typically, cement or other secure bonding material is utilized.

When it is desired to remove the crown, for any of various reasons, a channel twist drill 28 is utilized to form a channel 30 which extends entirely through the length of the crown until it reaches the tooth 24 therebeneath. Typically, it may be advisable to begin with a pilot hole twist drill and subsequently ream out that pilot hole by means of a larger channel twist drill.

After the channel is formed, a tap 32 is used to form an internal thread 34 within the channel 30 in the crown 22. After the entire channel has been suitably threaded, a tool extractor 36 is threaded into the channel and is continuously rotated until it abuts the upper surface 38 of the tooth 24. Continued rotation of the tool 36 causes the bond provided by the layer 26 to break so that some sections 40 remain adhered to the crown while other sections 42 will adhere to the tooth. However, the crown 22 will be freed from the tooth 24 and will remain intact.

The tooth or crown can then be attended to. For example, if the reason for removal of the crown was to permit attending to dental requirements of the teeth, this can be attended to before replacement of the crown. Alternately, it may be necessary to repair portions of the crown or other procedures. However, when such procedures are completed, the crown 22 can then be replaced back onto the tooth 24 by means of a new bonding layer 44.

The key 10, as shown in FIGS. 1 and 2, is inserted into the threaded channel 30 to fit into and plug up such channel. In this way, the hole previously formed in the crown will not serve to permanently disqualify utilization of the crown, but on the other hand maintains the crown so that it can be utilized as a removable crown. While the crown is in service on the tooth, the key forms part of the crown and will actually serve as a portion of the crown. However, should it be necessary to further remove the crown, the key can be extracted and the threaded channel is readily available for further removal.

Figure 7:
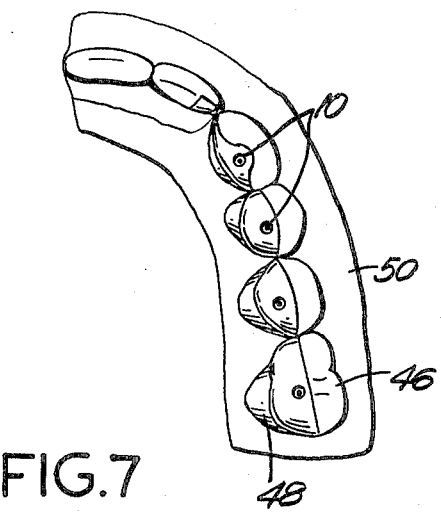
FIGS. 7-9 show various steps in the removal of a dental corwn where the dental crown was initially constructed having the removal capabilities of the present invention.
Figure 8:
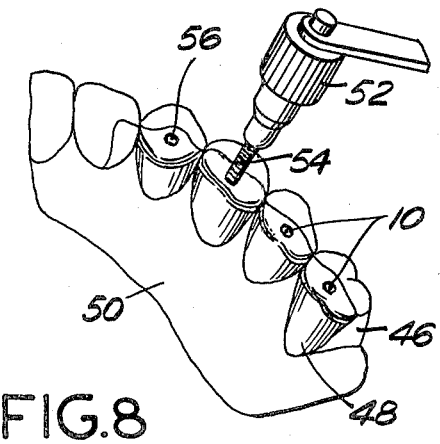
Figure 9:
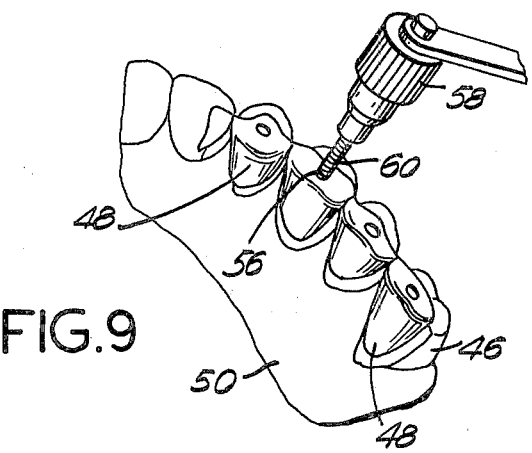

Referring now to FIGS. 7-9, there will be described the method of removal of a crown where the keys have already been inserted therein. As shown in FIG. 7, a plurality of teeth 46 are shown covered by a prosthesis 48, shown as a bridge utilizing removable crowns. The bridge extends over a number of teeth supported in the mouth area 50. Each of the crowns includes a key 10 inserted in the occlusal surface thereof. Such keys may have been initially inserted by casting them directly within the crown at the time of the construction of such crowns. Alternately, they may have been inserted subsequent to the actual formation of the crown by means of forming channels in the crowns and threading the channels and subsequently inserting such keys into such threaded channels.

Should it be desired to remove the bridge, as shown in FIG. 8, a suitable key wrench 50 is utilized having an extending bit 54 which can be inserted into the recess of the keys and utilized for extraction of the keys. As shown, the key has been extracted from the first of the crowns leaving the exposed threaded channel therein 56.

After the keys have been removed, a tool extractor 58, as shown in FIG. 9, is utilized together with its extracting bit 60, which is now threaded into the exposed threaded channels 56 in the crowns. Continuous rotation of the bit 60 into the threaded channels 56 will cause the bit 60 to reach the tooth and then break the bonding layer between the crown 48 and the teeth 46 there beneath. After suitable dental corrections are carried out as are needed, the bridge can then be replaced onto the tooth with additional keys inserted into the channels.

One of the benefits of utilizing the present system is that it is safer than utilizing small screws, Using prior art mechanisms, small screws must be manipulated in the patient's mouth and they are prone to being dropped causing medical problems to the patient. In the present situation, the recess provided in the key is deep, as shown in FIGS. 1 and 2, and accordingly, the key wrench inserted into the key is one that will retain the key in place so that it will not easily drop into the patient's mouth.

Figure 10A:
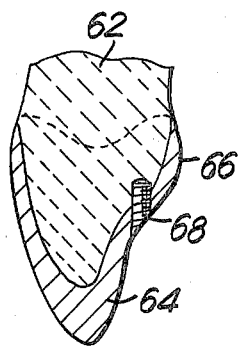
FIGS. 10A and 10B show schematically the utilization of the key in connection with an incline on an interior tooth.
Figure 11A:
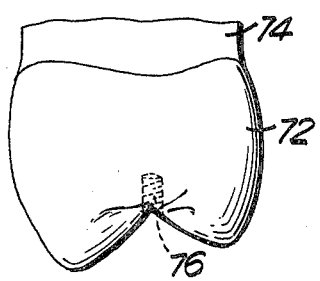
FIGS. 11A and 11B show schematically the utilization of a key in connection with an occlusal anatomy.
Figure 12A:
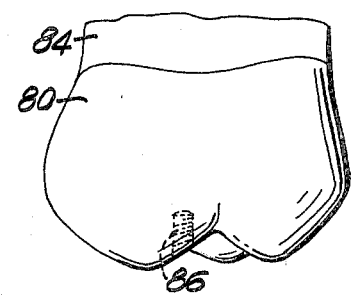
FIGS. 12A and 12B show schematically the utilization of a key in connection with an anatomical incline on a posterior tooth.
Figure 10B:
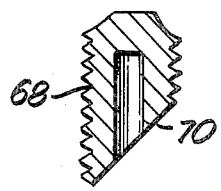

Another benefit of the present invention is that the key can be placed so that it can be modified to accommodate the particular type of tooth or the occlusal anatomy. For example, as shown in FIG. 10A there is shown an anterior tooth 62 on which is placed a crown 64 including the key 68 placed along the inclined side 66 of the tooth. The anatomy of the interior tooth is such that it has very little room for manipulation. However, although the key 68 should be placed parallel to the elongated axis of the tooth, the top portion of the key 68 can be configured to conform to the crown shape. Accordingly, as shown in FIG. 10B, the top surface 70 is shown to be angled a considerable amount from a horizontal plane in order to facilitate its inclusion in the outer surface of the crown.

Figure 11B:
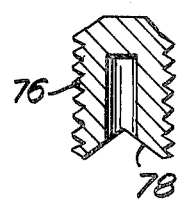

Similarly, as shown in FIG. 11B, with occlusal anatomy provided at the surface of the crown 72 placed on the tooth 74, the key 76 is again inserted and has its upper surface 78 configured, as shown in FIG. 11B to conform to such occlusal anatomy.

Figure 12B:
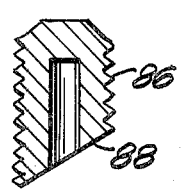

FIG. 12B shows the utilization of a crown 80 on a posterior tooth 84 where again the key 86 is placed on the surface and again has its outer upper surface 88 suitably configured to properly position it in the surface of the crown.

Accordingly, by utilizing the keys, a universal type of system is achieved which can be used in crowns on all type of teeth even in difficult areas such as anterior teeth and the incline of posterior teeth. Of course, the usual "fine tuning" of the crown required when the crown comes from the laboratory and prior to its being cemented into the mouth, can easily be accommodated for using the key of the present invention. If the occlusal anatomy has to be modified or carved, the present keys can easily accommodate such modification and still provide for all of their usual features.

The present system is workable with any type of material including gold, silver, palladium, porcelain, alloy, non-precious alloy, or any combination thereof. The only other extra step required would be the addition of a short length of rod or tube to be inserted vertically in the occlusal surface of extra hard type of non precious metal. This extra step is not required for any material other than the extra hard non-precious metal alloy. An optional procedure would be that the threads can be placed in the pattern from which the crown is made and be cast directly into the crown.

Also, since the present keys do not have to be initially cast in the tooth, but on the other hand can be subsequently formed in a threaded channel in the footh, there is no restrictive requirement that any part of the system has a melting-temperature higher than that of the gold alloys. The prior art system utilizing a cast sleeve requires this restrictive limitation on melting temperature.

Furthermore, the present system can be used on very short teeth or where there is limited occlusal clearance. Often teeth are very short, or it is not possible to reduce the occlusal height to have very much thickness of material on the occlusal or chewing surface of the crown. The present system can accommmdate this.

An additional feature of the present invention is that it can be used as a venting system during the cementation of the crowns. This allows for the escape of cement from the vent hole to allow the crown to be completed seated on the tooth. This is easily accomplished by having a small hole formed into the bottom of the key. During cementation, the trapped cement on the top of the tooth and under the crown is released during its fluid state through the opening in the key. After the cement is set, this special venting key is removed and replaced with a regular key.

Another feature is that the key can be used to provide additional retention capability. For example, a short or badly destroyed tooth that might have difficulty holding a crown could be assisted by use of the key. The key would extend through the crown and into the tooth in either a vertical or horizontal fashion so as to prevent the crown from being dislodged from the tooth. As a result, the key serves both as a plug for the treaded channel and as an assisting retention instrument.

Figure 13:
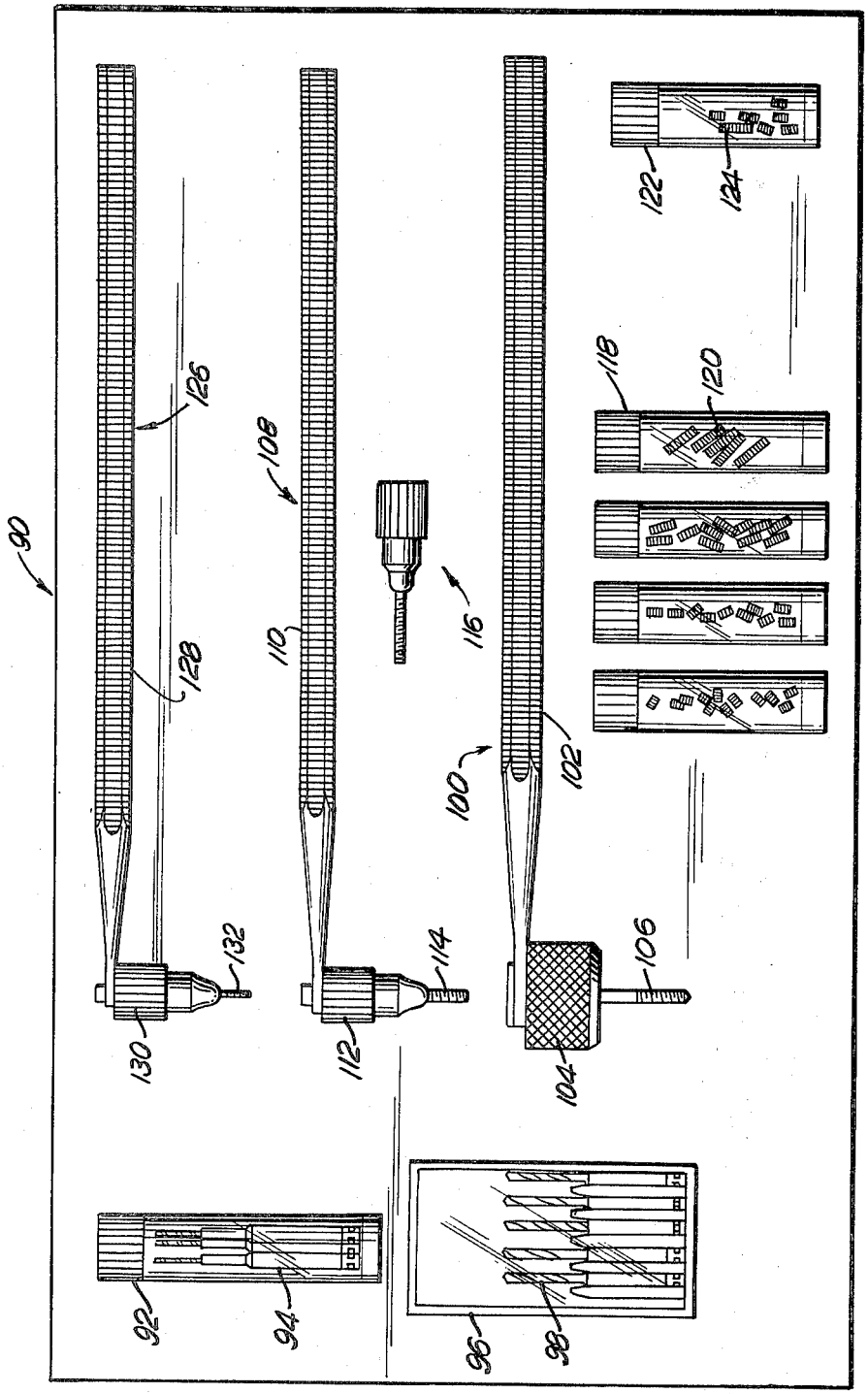
FIG. 13 shows a kit for tooth removal which can be utilized in a clinical environment.

Referring now to FIG. 13, there is shown a ket 90 containing all of the various instruments needed for the removal of a crown. The kit includes a container 92 in which there are a plurality of pilot hole twist drills 94 which can be used for initially forming the hole in the crown.

There is also provided a small container 96 containing channel twist drills 98 which are used after the pilot hole has been drilled in order to ream out the channel to a proper size. Once the channel has been formed, the tap instrument 100 is utilized to form the threads within the channel. The tap extractor includes a handle portion 102 extending from a knurled knob 104 which serves as the head for holding the tapping bit 106.

An extractor instrument 108 can then be inserted into the threaded channel for removal of the crown from the tooth. The extractor includes a handle portion 110 coupled to a splined head 112 which supports the extractor bit 114. An additional long extractor tool 116 is provided for alternate use with the extractor 108.

When inserting a key, the suitable sized key is taken from any of the various tubes 118 each of which contain a plurality of individual keys 120 of the type heretofore described. There is also provided an additional tube 122 having the venting keys 124 heretofore described, which includes the axial channel inserted through the bottom thereof.

The key wrench 126 is utilized for insertion and removal of such keys. The key wrench includes a handle portion 128 connected to a splined head 120 supporting the wrench bit 132. The key wrench inserts the bit 132 into the recess provided in the keys for extraction and insertion of the keys, as heretofore explained.

The particular kit described in FIG. 13 would be one that would find use in clinical work such as the dentist's office. All of the tools provided would be such as can be easily fit into the patient's mouth and manipulated in accordance with standard procedures.

Figure 14:
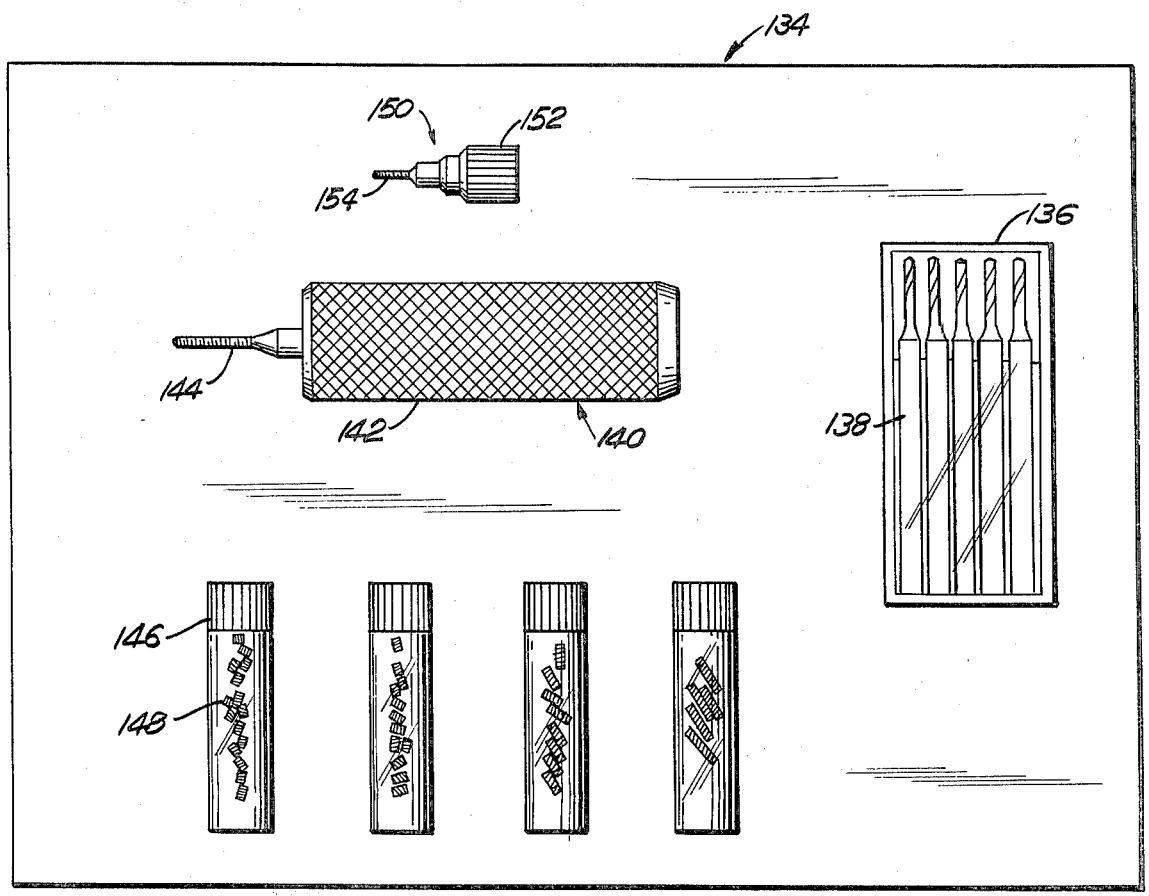
FIG. 14 shows a ket which can be utilized for installing the mechanism in crowns in a laboratory environment.

In the laboratory, some of the pieces of equipment can be modified since the laboratory does not work directly in a patient's mouth but on the other hand works from a model. For laboratory work, the kit shown in FIG. 14 could be utilized. Such kit, shown generally at 134 includes a container 136 having a number of channel twist drills 138 for forming the channels in the tooth. A hand held tap 140 is provided for threading the channel. The tap includes a knurled handle 142 having an axially extending bit 144 extending therefrom. A plurality of containers 146 are provided, each of which hold an assortment of individual keys 148, of the type heretofore described. A hand held key wrench 150 is also included having a splined head 152 supporting an axially extending bit 154 extending therefrom.

Figure 15A:
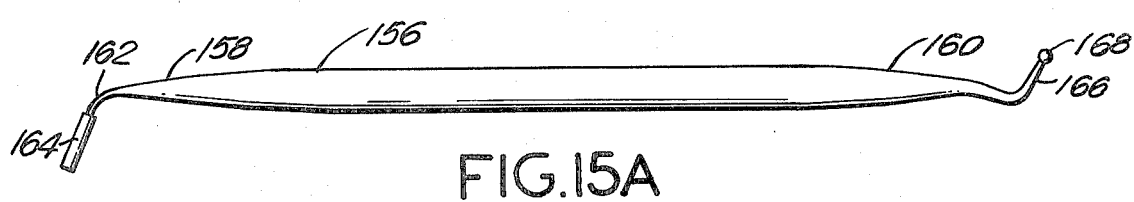
FIGS. 15a, b, and c, show portions of an additional guide instrument for use in connection with the present invention.
Figure 15B:
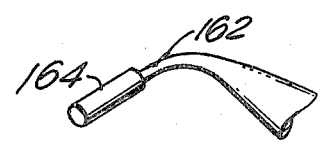
Figure 15C:

FIG. 15a shows a side view of a preparation guide instrument which can be utilized in connection with the present invention. The instrument comprises a body portion 156 typically formed of metal material and having tapered opposing ends 158, 160. At the left end an arm 162 extends in a downward direction to support a cylindrical tool section 164, which can better be seen in FIG. 15b. At the opposing end, the arm 166 extends upwardly and supports a spherical tool section 168, which can best be seen in FIG. 15c.

The cylindrical tool section 164 is formed of sufficient diameter to allow for the threads of the described system to be placed into the crown. For example, when preparing or reducing an anterior tooth for a crown, there is first provided a flat plateau or niche which can be cut on one side of the tooth. This can best be seen by referring to FIG. 10A. The area of the tooth around the key 68 is prepared or cut from the tooth. The preparation guide instrument 156 can then be used by inserting the cylindrical end portion 164 as a gauge to verify that sufficient tooth structure has been removed for proper construction of the crown.

The right handed end of the tool, and specifically the spherical section 168, has a thickness which is approximately the same as one of the keys, and specifically the shortest key. This end is used as a gauge to judge as to whether sufficient reduction of the tooth has been made between it and the opposing tooth in the other arch.

This can best be understood by referring back to FIG. 6. After the tooth has been reduced, this end of the instrument would be held on the tooth in the area where the keys are to be placed. The patient can then close the mouth with the instrument in place to judge if there is sufficient clearance for the key.

There has been disclosed heretofore the best embodiment of the invention presently contemplated. However, it is to be understood that various changes and modifications may be made thereto without departing from the spirit of the invention.

I claim:

1. A removable dental crown adapted to be secured by a layer of bonding material to a tooth, said crown having a removable key threadedly secured in a channel formed directly in the top portion of the crown and said key forming an integral part of the crown during actual usage of the crown, said key having a recess therein for receiving a tool for the removal of said key thereby leaving a threaded channel in said crown for threadably receiving an extractor tool therein for engagingly breaking said bonding layer and forcing the crown away from the tooth.

2. A removable dental crown as in claim 1, wherein said key comprises a set screw having a wrench receiving recess therein.

3. A removable dental crown as in claim 2, wherein said set screw comprises a cylindrical body externally threaded end to end.

4. A removable dental crown as in claim 3, wherein said recess comprises a counter-sunk bore axially extending into an upper end thereof.

5. A removable dental crown as in claim 4 and further comprising a channel axially extending into a lower end of said cylindrical body.

6. A removable dental crown as in claim 3, wherein one end of said cylindrical body is subsequently flat and the other end is shaped to a suitable configuration.

7. A removable dental crown as in claim 3, wherein an upper end of said cylindrical body extends to the surface of the crown and conforms in shape to the crown configuration.

8. A removable dental crown as in claim 4, wherein said recess extends to a depth of at least ½ of the height of the cylindrical body.

9. A method for removing a dental crown secured by a layer of bonding material to a tooth, said method comprising the steps of:
   forming a cylindrical channel directly into the dental crown;
   tapping the channel in the crown using a non-tapered tap; removing the tap, and
   threading extractor tool into the tapped channel until the bonding layer breaks and frees the crown from the tooth.

10. A method as in claim 9, and further comprising the steps of inserting a key into the tapped channel and maintaining it in place as an integral portion of said crown during actual usage of the crown and until removal of the crown is desired, and removing the key so that the extractor tool can be threaded into the channel.

11. A method as in claim 10, wherein said key comprises a set screw having a recess, and wherein said step of removing the key comprises inserting a key wrench into the recess and withdrawing the set screw.

12. A method as in claim 9, and further comprises the step of casting a set screw housing into the dental crown to form said channel.

13. A method as in claim 10, wherein said key extends to the occlusal surface of the crown and further comprising the step of adjusting the occlusal configuration including said key, as is needed to fit the patient requirements.

14. A method as in claim 10, wherein said key is inserted so that it extends to the tooth and is embedded therein for retaining the crown to the tooth.

* * * * *